US008697151B2

(12) United States Patent
Contet-Audonneau et al.

(10) Patent No.: US 8,697,151 B2
(45) Date of Patent: Apr. 15, 2014

(54) **USE OF AN EXTRACT FROM THE *VIGNA ACONITIFOLIA* PLANT IN A COSMETIC AND/OR DERMOPHARMACEUTICAL COMPOSITION**

(75) Inventors: Jean-Luc Contet-Audonneau, Saint-Max (FR); Louis Danoux, Saulxures les Nancy (FR); Véronique Gillon, Essey-les-Nancy (FR); Gilles Pauly, Nancy (FR); Philippe Moser, Essey-les-Nancy (FR)

(73) Assignee: BASF Beauty Care Solutions France S.A.S., Lyon (FR)

( * ) Notice: Subject to any disclaimer, the term of this patent is extended or adjusted under 35 U.S.C. 154(b) by 375 days.

(21) Appl. No.: 12/581,564

(22) Filed: Oct. 19, 2009

(65) Prior Publication Data

US 2010/0273717 A1   Oct. 28, 2010

Related U.S. Application Data

(63) Continuation of application No. 10/494,744, filed as application No. PCT/EP02/12148 on Oct. 31, 2002, now abandoned.

(30) Foreign Application Priority Data

Nov. 9, 2001   (EP) .................................... 01402887

(51) Int. Cl.
    *A61K 36/48*    (2006.01)
(52) U.S. Cl.
    USPC ........................................................ 424/757
(58) Field of Classification Search
    CPC .................................................... A61K 36/48
    See application file for complete search history.

(56) References Cited

U.S. PATENT DOCUMENTS

| 4,172,887 | A |   | 10/1979 | Vanlerberghe et al. |
| 5,270,200 | A |   | 12/1993 | Sun et al. |
| 5,322,839 | A |   | 6/1994  | Voegeli et al. |
| 5,705,169 | A |   | 1/1998  | Stein et al. |
| 5,730,960 | A |   | 3/1998  | Stein et al. |
| 5,830,887 | A |   | 11/1998 | Kelly |
| 5,945,091 | A |   | 8/1999  | Habeck et al. |
| 6,004,558 | A | * | 12/1999 | Thurn et al. ................ 424/757 |
| 6,193,960 | B1 |  | 2/2001  | Metzger et al. |
| 6,500,470 | B1 |  | 12/2002 | Pauly |

FOREIGN PATENT DOCUMENTS

| DE | 1165574    | 8/1960 |
| DE | 2024051    | 12/1971 |
| DE | 19712033   | 9/1998 |
| DE | 19756377   | 6/1999 |
| EP | 0693471    | 1/1996 |
| EP | 0694521    | 1/1998 |
| EP | 0818450    | 1/1998 |
| FR | 2252840    | 6/1975 |
| FR | 2796839    | 2/2001 |
| GB | 0962919    | 7/1964 |
| GB | 1333475    | 10/1973 |
| GB | 1494915    | 11/1974 |
| JP | 05-230100  | 9/1993 |
| JP | 07-506822  | 7/1995 |
| JP | 2002-507575 | 3/2002 |
| JP | 2002541082 | 12/2002 |
| WO | WO 03/039442 | 5/2003 |

OTHER PUBLICATIONS

Kadam et al. "Nutritional Composition, Processing and Utilization of Horse Gram and Moth Bean". CRC Crit. Rev. in Food Sci. Nutr. vol. 22, No. 1 (1985) 1-26, particularly pp. 12, 17 and 21.*
Kadam, S.S. et al., "Nutritional Composition, Processing, and Utilization of Horse Gram and Moth Bean,". CRC Crit. Rev. in Food Sci. Nutr. 22(1) pp. 1-26, (1985).
Loden, M., et al., "Instrumental and Dermatologist Evaluation of the Effect of Glycerine and Urea on Dry Skin in Atopic Dermatitis," Skin Res Tech, 7, pp. 209-213 (2001).
Bradford, M. M. et al., "A Rapid and Sensitive Method for the Quantitation of Microgram Quantities of Protein Utilizing the Principle of Protein-Dye Binding," Anal. Biochem. 72, pp. 248-254 (1976).
Hissin, P. J., et al., "A Fluorometric Method for Determination of Oxidized and Reduced Glutathione in Tissues," Analytical Biochemistry, 74, pp. 214-226 (1976).
Denizot, F., et al., "Rapid Colorimetric Assay for Cell Growth and Survival Modifications to the Tetrazolium Dye Procedue Giving Improved Sensitivity and Reliability." J. of Immunological Methods. 89. pp. 271-277 (1986).
Henseleit, U., et al., "Induction of Apoptosis in Human HaCaT Keratinocytes," Arch Dermatol Res, 288, pp. 676-683 (1996).
Parat, M. O., et al., "Zinc and DNA Fragmentation in Keratinocyte Apoptosis: Its Inhibitory Effect in UVB Irradiated Cells," J. or Photochemistry and Photobiology B: Biology, 37, pp. 101-106 (1997).
Falbe, J., "Surfactants in Consumer Products," Springer-Verlag, Berlin, pp. 54-125 (1987).
Lockhead, R. Y., et al., "Encyclopedia of Polymers and Thickeners for Cosmetics," Cosmetics & Toiletries, 108, pp. 95-135 (1993).
Borhade, V. P., et al., "Solubilization and Functioanl Properties of Moth Bean" Journal of Food Biochemistry, 8:3, pp. 229-235 (1984) XP-002196636.
Todd, C., et al., "Volatile Silicone Fluids for Cosmetic Formulations," Cosmetics and Toiletries, 19, pp. 29-32 (1976).
Vigna aconitifolia (Jacq.) Marechal, http://www.hear.org/gcw/html/autogend/species/20205.HTM accessed Jul. 27, 2005.
Vigna trilobata (L.) Verdc. http://www.hear.org/gcw/html/autogend/species/20226.HTM accessed Aug. 5, 2005.
Whyte, R. O. et al., "Legumes in Agriculture," FAO Agriculture Studies No. 21, pp. 302-303 (1953).
"Glycerol," Wikipedia, the free encyclopedia, pp. 1-4 http://en.wikipedia.org/wiki/Glycerol accessed Nov. 22, 2006.
Lawn, R. J., "The Asiatic Vigna Species," Evolution of Crop Plants, Library of Congress, pp. 321-326 (1995).
Source: Agricola database 1970-1996, Australian New Crops, "Listing of Useful Plants of the World," pp. 1-9 (1996).

(Continued)

Primary Examiner — Amy L Clark
(74) Attorney, Agent, or Firm — Servilla Whitney LLC

(57) ABSTRACT

An active composition for treating skin having a protein-containing extract from a *Vigna aconitifolia* plant.

19 Claims, No Drawings

(56) References Cited

OTHER PUBLICATIONS

Vit-A-Like, "Efficacy Tests on the Epidermis," Laboratoires Serobiologiques Division of Cognis France, pp. 4-7 (2007).
International Search Report, dated Mar. 20, 2003.
"Kosmetische Farbemittel", *3rd Edition, VCH Verlagsgesellschaft mbH, D-6940 Weinheim (Federal Republic of Germany)* 1991, 81-106.
Falbe, et al., "Katalysatoren, Tenside und Mineraloladdive", *George Thieme Verlag Stuttgart* 1978, 123-217.
Finkel, P., "Formulierung Kosmetischer Sonnenschutzmitel", *SOFW-Journal, 122* 1996, 543-548.
Finkel, P., "Formulierung Kosmetischer Sonnenschutzmittel", *Parfumerie und Kosmetik 80* 1999, 10-16.
Seigneurin, D. et al., "L'antigene Ki-67, Marqueur Du Cycle Cellulaire et de la Proliferation Tumorale", *Pathologie Biologie 39:10* 1991, 1020-1028.
Vasseur, et al., "Appreciation de la Cytotoxicite Par La, Mesure De LA.T.P.", *J. Francias d'Hydrologie, 3(27)* 1978, 149-155.

\* cited by examiner

USE OF AN EXTRACT FROM THE *VIGNA ACONITIFOLIA* PLANT IN A COSMETIC AND/OR DERMOPHARMACEUTICAL COMPOSITION

CROSS REFERENCE TO RELATED APPLICATIONS

This application is a Continuation of application Ser. No. 10/494,744, filed May 7, 2004, which is the National Stage entry of PCT/EP02/12148, filed Oct. 31, 2002, which claims priority to European patent application number EP 01402887.2, filed Nov. 9, 2001, all of which are incorporated herein by reference in their entireties.

BACKGROUND OF THE INVENTION

This invention relates generally to cosmetic and dermopharmaceutical products and, more particularly, to the use at least one protein-containing extract of the *Vigna aconitifolia* plant. The present invention also relates to cosmetic and/or dermopharmaceutical preparations containing such an extract.

In the search for new food sources for developing countries, attention has been drawn to the forms of the undemanding and drought-resistant seeds of *Vigna aconitifolia* [Jacq] Marechal (Fabaceae), or moth bean, cultivated in Sri Lanka, the Himalayas, Burma, Sudan and East Africa. Whereas the cooked, dry seeds of *Vigna aconitifolia* have little nutritional value, the pods are widely used as a food source.

The content of the seeds is, on average, 61.9% carbohydrates, 21.9% proteins, 3.48% lipids, 1.3% polyphenols and 0.65% phytic acid. In an overview by Kadam and Salunke [S. S. Kadam, D. K. Salunkhe, Nutritional composition, processing and utilization of horse gram and moth bean, CRC Critical reviews in Food Science and Nutrition, 1985, 1-26], the authors report on the presence of other ingredients, such as trypsin inhibitors and alpha-amylase inhibitors.

Whereas seed extracts of other, less common *Vigna* species, such as *Vigna trilobata*, are known to have a caring and healing effect (cf. French patent application FR 2796839 A1), hitherto only a dietetically restorative effect in fever patients has been attributed to Vigna aconitifolia seeds.

Protein fractions of the seeds of leguiminosae, more particularly soy and lima beans, are disclosed in U.S. Pat. No. 5,322,839 as active components with anti-inflammatory, elastase-inhibiting and trypsin-inhibiting properties.

However, there is an increasing demand on the cosmetic and pharmaceutical market for vegetable active components which would have, for example, caring, anti-ageing and revitalizing effects on the skin. In addition, the composition of the product would have optimal dermatological compatibility, so that even sensitive consumers would not react with irritation. The active components in question would also perform other functions which, at the same time, would positively influence or at least would not diminish the technical properties of the cosmetic product, such as storage stability, light stability and formulation behavior.

Accordingly, the complex problem addressed by the present invention was to find new effects of already known plants and to enable these extracts to be used in cosmetic and/or dermopharmaceutical preparations which would be distinguished by high compatibility, even for sensitive skin, and also by high physicochemical stability.

DETAILED DESCRIPTION OF THE PREFERRED EMBODIMENTS

The present invention relates to the use of a protein-containing extract extracted from the plant *Vigna aconitifolia* for the production of cosmetic and/or dermopharmaceutical preparations for local application to the skin, the epithelial appendages and/or the mucosa.

The present invention also relates to cosmetic and/or dermopharmaceutical preparations for local application which contain a protein-containing extract of the plant *Vigna aconitifolia*.

It has surprisingly been found that the protein extracts of *Vigna aconitifolia* produce particular biological effects when locally applied to the skin, the epithelial appendages and the mucosa and show very high tolerance and that the use as an active component—individually or in conjunction with at least one other active component—of at least one protein fraction extracted from *Vigna aconitifolia* in a composition or a cosmetic or dermopharmaceutical product for local application to the skin, the epithelial appendages and/or the mucosa enables regenerative effects, anti-irritation effects, anti-ageing effects and growth-promoting activity to be obtained.

The protein-containing extracts of *Vigna aconitifolia* are particularly suitable for the preventative and curative treatment of sensitive skin types. They are excellently tolerated. In human in vivo tests, it was found that even a small dose of *Vigna aconitifolia* extracts in the locally applied preparations was sufficient to produce a distinctly increased cell renewal rate in the human epidermis. The protein fractions of *Vigna aconitifolia* seeds in particular show such properties as pronounced stimulation of cell growth and metabolism (energy-giving, stimulating, anti-ageing activity), marked anti-apoptosis activity, protective activity against oxidative stress in conjunction with the anti-apoptosis activity, regenerating and revitalizing activity and acceleration of the epidermal cell renewal cycle.

Active components in the context of the present invention are understood to be extracts of the plant *Vigna aconitifolia*, more particularly extracts of *Vigna aconitifolia* seeds. Pronounced effects are attributed in particular to the protein fractions of the plant extracts and preferably to protein fractions of *Vigna aconitifolia* seeds. Among the extracted fractions which form the active component, compositions which contain at least two protein fractions or at least one soluble protein fraction are particularly preferred.

The protein-containing extracts may readily be incorporated in conventional formulations in combination with other auxiliaries, such as polyols, antioxidants and preservatives, so that the formulations show good physicochemical stability.

The extracts or soluble protein fractions according to the invention may also be incorporated in, or combined with, any other relevant cosmetic vector, for example film formers, liposomes, cyclodextrins, micelles, macro-, micro- and nanoparticles and macro-, micro- and nanocapsules, or may be adsorbed or grafted onto organic polymers or mineral supports.

Examples Demonstrating the Properties of the *Vigna aconitifolia* Protein Extracts The biological properties and activities of the *Vigna aconitifolia* protein extracts were determined and measured by tests which are known to the expert and of which the results are presented in the following:

1. Cell Growth and Survival Test

There are key markers for evaluating cell activity, including ATP, proteins and glutathione.

ATP (adenosine triphosphate) is a cell constituent which stores energy and which is mainly produced in mitochondria. Cells need ATP to ensure the activity of their enzymes which in turn control the cytoskeleton, the ion channels, food uptake and many vital biological processes of the cell (Vasseur, P., Aerts., C. "Appréciation de la cytotoxicité par la mesure de l'ATP. Journal français Hydrologie (1982), vol. 9, pp. 149-156).

The protein concentration of the cells was determined by the Bradford method (Bradford, M. M., A rapid and sensitive method for the quantification of microgram quantities of protein utilizing the principle of protein-dye binding. Anal. Biochem. (1977), vol. 72, pp. 248-254).

Glutathione (GSH) is a peptide produced by cells to protect the cell against oxidative stress or heavy metals, for example lead or mercury. The three amino acids involved in the reduced form of GSH are attached to specific cytoplasmatic enzymes which consume ATP. Controlling the GSH level has a positive effect on the activity of glutathione-S-transferase which is a detoxifying enzyme. GSH was determined by Hissin's method (Hissin, P. J., Hilf, R.: A fluorometric method for determination of oxidized and reduced glutathione in tissues. Analytical Biochemistry (1977), vol. 74, pp. 214-226).

1a) Effects on Cell Growth (Table 1a)

Human fibroblasts were incubated with 10% foetal calf serum (Dutcher) in a nutrient medium (DMEM=Dulbecco Minimum Essential Medium from Life Technologie S.a.r.l.) and incubated for 24 hours at 37° C. in a 5% $CO_2$ atmosphere.

The growth medium was then replaced by a sub-optimum medium (with SVF) which contained various concentrations of extracts (0; 0.1 and 0.3% by weight/volume) according to the description of the invention. After incubation for 3 days at 37° C., growth was evaluated by measurement of the cell protein content and the intracellular ATP content.

1b) Effects on Survival (Table 1b)

The fibroblast test is conducted to the same protocol as the growth test, but with a first incubation period of 3 days.

Survival was evaluated by measuring the following contents:

metabolized MTT (methyl thiazolyl tetrazolium) rate

The activity of the mitochondria is determined by the MTT test. MTT is reduced to formazane by an enzyme of the respiratory chain, succinate dehydrogenase (Denizot, F., Lang, R.: Rapid colorimetric assay for cell growth and survival. J. Immunol. Methods, 89, 271-277, 1986).

proteins, glutathione (GSH), a peptide produced directly by the cell for controlling oxidative stress or various contaminants, for example heavy metals. Its synthesis needs ATP as an energy source.

Tests 1a and 1b were carried out as triple determinations and were repeated twice or three times. The *Vigna aconitifolia* extracts used in various concentrations were prepared by the process of Example 7.

The results are converted into a ratio to a reference value for protein, ATP, MTT and GSH and expressed as a percentage in relation to the untreated control (extract-free formulation) as a mean value+/−SEM (mean error).

TABLE 1a

Growth Test
Results in % based on the control without extract
(mean value of 2 triple assays)
Vitoptine ® (Vigna aconitifolia extract,
Laboratoire Sérobiologique, Pulnoy)

| Concentration of active component (Vitoptine ®) % by wt./vol. | Proteins | ATP |
|---|---|---|
| 0 | 100 | 100 |
| 0.1 | 107 | 113 |
| 0.3 | 110 | 114 |

The results in Table 1a in the form of the protein content and ATP content show a distinct capacity of Vitoptine® to increase the growth of human fibroblasts in in vitro cultures, even in doses of 0.1% (weight/volume). The values represent the cells counted and ATP contents determined for various concentrations.

TABLE 1b

Cell Survival Test
Results in %, based on the control without extract
(mean value of 3 triple assays)

| Concentration of the active component (Vitoptine ®) % wt./vol. | MTT | Proteins | GSH/proteins |
|---|---|---|---|
| 0 | 100 | 100 | 100 |
| 0.1 | 100 | 107 | 101 |
| 1 | 111 | 118 | 122 |

The values in Table 1b show a distinct increase in the MTT, protein and GSH contents for 1% by wt./vol. Vitoptine® and are thus proof of the revitalizing and regenerating properties of the extract.

These results show that the active components based on the protein extract of *Vigna aconitifolia* are highly active in improving growth and the metabolism (synthesis of ATP, the proteins and glutathione) by human fibroblasts which clearly reflects an energy-giving, stimulating and "anti-ageing" activity of these extracts.

2. Anti-Apoptosis Test

Apoptosis is a biological, active process used by living organisms to eliminate certain cells of their tissue by autolysis, more particularly destruction of the proteins and the nuclear DNA into small fragments which are salted out into the cytoplasm. Apoptosis can also be induced by oxidative stress (UV-R, inflammation), by a lack of growth factors or by toxic substances (contaminants, genotoxic substances . . . ).

By removing the corresponding factors which send survival messages to the cells, the suicide program can be started and apoptosis initiated. Subsequent determination of the cell counts provides information on the extent of the cell death initiated. The system is thus the most suitable for monitoring the effect of anti-apoptosis components. The process may be applied both to ex-vivo and to in-vitro cultures of skin cells (fibroblasts, keratinocyes, epithelial cells) and to ex-vivo cultures of human hair follicles.

Demonstration of Apoptosis and Determination of the Content of Apoptotic Cells—In Vitro In the course of apoptosis, fragments of the DNA strands present in the cell nucleus are split off by the attack of endonucleases and released into the cytoplasm. As described, for example, by Henseleitet et al. in Archiv. Dermatol. Res. 288 (11), 676 (1996) or Parat et al. in J. Photochem. Photobiol B. Biol. 37, 101 (1997), the apoptosis level can be determined, for example by the ELISA method.

The ability of the *Vigna aconitifolia* extracts to prevent apoptosis induced by a lack of growth factors in human skin cells was investigated. This test was carried out in vitro on human fibroblasts (test 2a) and human keratinocytes (test 2b). The human cells were cultivated in a nutrient medium (DMEM=Dulbecco Minimum Essential Medium from Life Technolgie S.a.r.l.) containing 10% foetal calf serum (FCS=foetal calf serum from Dutcher). Bromodeoxyuridine (BrdU) was added to this nutrient medium; it was incorporated in the DNA and later used to detect the DNA fragments in the cytoplasm. After incubation for 3 days, the cells received a survival medium (DMEM) without serum or growth factors, which contained various concentrations (0; 0.05; 0.1% weight/volume) of the Vitoptine® contents to be tested, and were incubated for 2 days at 37° C. After incubation, the cells were recovered by trypsinization and then analyzed.

Assay of the Apoptotic Cell Content

In this method, the cells (not the cell nucleus) are lysed and the apoptotic cell content is assayed by an ELISA test which discloses BrdU that was incorporated in the cytoplasmic ADN fragments.

The results are expressed as a percentage in relation to the control (Henseleit, U., Rosenbach, T., Kolde, G.: "Induction of apoptosis in human HaCaT keratinocytes"; Archiv. Dermatol. Res. (288) 22, 676-683, 1996).

TABLE 2a

Anti-apoptosis activity of Vitoptine ® on human fibroblasts by comparison with extract-free medium (mean value of 4 triple assays).

| Concentration (% by wt./vol.) | Cell count | Level of cytoplasmic DNA fragments |
|---|---|---|
| Control | 100 | 100 |
| 0.05 | 105 | 78 |
| 0.1 | 106 | 74 |

TABLE 2b

Anti-apoptosis activity of Vitoptine ® on human keratinocytes by comparison with extract-free medium (mean value of 4 triple assays).

| Concentration (% by wt./vol.) | Cell count | Level of cytoplasmic DNA fragments |
|---|---|---|
| Control | 100 | 100 |
| 0.05 | 102 | 39 |
| 0.1 | 105 | 46 |

The results in Tables 2a and 2b show a distinct reduction in the apoptosis level for keratinocytes and fibroblasts after treatment with Vitoptine® protein extracts.

The *Vigna aconitifolia* extracts (Vitoptine®) according to the invention are well capable of reducing the apoptosis levels induced in a nutrient medium of human cells by removing the growth factor which explains the ability of these extracts to control the ageing of tissue by a growth-factor-like effect (growth factor effect). Vitoptine® is particularly suitable for use an anti-ageing component.

3. Demonstration of Apoptosis and Determination of the Apoptotic Cell Content—Ex Vivo The TUNEL technique (Tdt-mediated UTP nick end labelling, Boehringer) was used with a detection kit for in vitro cell death for the determination of apoptotic cell nuclei. It is suitable for determining the apoptosis level via the detection of structural changes in the cell nuclei.

Another technique uses an immunohisothemical technique of special antibodies against Ki 67, a marker for the mitotic activity of the cells (Seigneurin D., Guillaud Ph; l'antigéne Ki 67, marqueur du cycle cellulaire et de la proliferation tumorale, Pathol. Biol. 39, 10, 1020-1028, 1991).

A CLSM microscope (confocal laser scanning microscope) was used for optical quantification. The micrographs taken were quantified by image analysis. The intensity of the reaction was expressed by a coefficient that is proportional to the area examined.

Preparation of the Human Cells

Apoptosis was initiated by addition of a basic culture medium prepared by dilution of DMEM in Hanks Medium. Human skin explantates from surgical operations were cultivated in Hanks Medium containing 10% by weight DMEM (DMEM=Dulbecco Minimum Essential Medium). Two applications of a cream in a quantity of 2 mg/cm$^2$ were made on the first and third day. The explantate was then incubated for 7 days at 37° C./5% $CO_2$.

After histological preparation, the TUNEL technique was used for epidermal vertical sections and mitosis studies with Ki 67 on horizontal sections.

TABLE 3a

Mitosis activity (Ki 67) after treatment with Vitoptine ® in an ex vivo test (mean value of 5 tests)

| | Particle count/ epidermal area |
|---|---|
| Control before determination (D0) - without apoptosis | 841.15 |
| Control without treatment D7* - with apoptosis | 157.95 |
| Placebo cream D7* | 120.9 |
| Cream with active component 1% D7* | 175.9 |
| Cream with active component 3% D7* | 221.25 |

*after incubation for 7 days in Hanks Medium containing 10% DMEM

TABLE 3b

Anti-aptosis activity of Vitoptine ®-treated human epidermis - apoptosis (TUNEL) determination in an ex vivo test (mean value of 5 tests)

| | Particle count/ epidermal area |
|---|---|
| Control before determination (D0) - without apoptosis | 87.3 |
| Control without treatment D7* - with apoptosis | 89.5 |
| Placebo cream D7* | 99.1 |
| Cream with active component 1% D7* | 13.5 |
| Cream with active component 3% D7* | Non-detectable |

*after incubation for 7 days in Hanks Medium containing 10% DMEM

Comparison of the control D0 with D7 is verification of the method and shows that a distinct apoptosis-controlled dying off of the cells can be detected by the methods. However, a major increase in mitosis activity and a distinct reduction in apoptosis activity were observed when Vitoptine®-containing preparations were used. This is a reflection of a strong anti-ageing effect.

4. Epidermal Cell Renewal Activity Test

Determination of the Stimulation of Epidermal Cell Renewal In Vivo by the Dihydroxyacetone Test (DHA Test)

Comparative in vivo tests were conducted to determine the accelerated epidermal cell renewal activity using 5 emulsions containing 0.2% by weight or 0.5% by weight vitamin A palmitate, 3% by weight or 5% by weight VITOPTINE® (extract of *Vigna aconitifolia*, Lab. Sero., Pulnoy) versus placebo.

Composition of the Emulsions:

| Phase A | |
|---|---|
| Cetearyl alcohol and Ceteareth-20 | 5 |
| Glyceryl stearate and PEG-100 stearate | 3.5 |
| Glyceryl stearate | 2.5 |
| Cetearyl alcohol | 2 |
| Octyl dodecanol | 5 |
| Paraffin | 3 |

-continued

| Phase B | |
|---|---|
| LS stabilizer (methylparaben, 58.2% - Dipotassium EDTA, 30.6% - Hexamidine diisethionate, 11.2%): | 0.3 |
| Aqua conservata | to 100 |

| Phase C |
|---|
| Active components |

Phase A and phase B were heated to 75° C. The aqueous phase was added to the fatty phase with continuous stirring and cooled to 60° C. by continued stirring. The combined phases were then homogenized for 2 mins. with an Ultraturrax. Finally, the active component is added with stirring and the whole is cooled to room temperature.

Study Procedure

The study was carried out as a double blind study involving 12 female volunteers aged between 18 and 55 years.

The measurement parameter was the intensity of tanning of the skin after pigmenting with dihydroxyacetone. The decreasing tanning intensity corresponds to an increase in the renewal of the stratum corneum and the rate of the epidermal cell renewal cycle.

Eight areas (two groups of four) on the inside of the lower forearm were selected:
control area untreated and unpigmented by DHA,
area treated with placebo cream,
area treated with cream containing vitamin A palmitate
area treated with cream containing VITOPTINE®.

A standardized and randomized pretreatment with 3 mg/cm² of a preparation was carried out daily for 7 days. After the pretreatment, on day 8, DHA in the form of a face and body tanning lotion containing 5% by weight DHA was applied to the control and treated areas by an occlusive standardized process. On day 9, the occlusive plasters were removed. This was followed for another 6 days (days 10 to 15) by the same treatment as on days 1 to 7. The color intensity of the skin was determined immediately after removal of the plasters and 6 days later by colorimetric measurements (Minolta chromameter) via luminescence.

Results

TABLE 4

Epidermal cell renewal in an in vivo test on 12 volunteers - comparison of the effectiveness of vitamin A palmitate and Vitoptine ® versus placebo

| | | | D 15 | | | | |
|---|---|---|---|---|---|---|---|
| | | | | Cream containing vitamin A | | Cream containing Vigna aconitifolia protein extract | |
| | DHA pigmenting | Mean value | Mean value placebo | | | | |
| Parameter | day 9 (D9) | controls | cream | 0.2% | 0.5% | 3% | 5% |
| Luminescence (AU) | 58.65 | 61.33 | 62.13 | 62.18 | 62.44 | 62.72 | 62.79 |
| Development of luminescence (D15-D9) | | 2.68 | 3.48 | 3.53 | 3.79 | 4.07 | 4.14 |
| Development of luminescence (D15-D9) % referring to control area | | | 30 (ns) | 32 (ns) | 41 (ns) | 52 (*) | 54 (**) |

D9: immediately after removal of the plasters
D15: 6 days after removal of the plasters
AU: arbitrary unit
In the Wilcoxon T Test (ns) not significant (*) p = 0.05 (**) p = 0.04

The first calculation (D15-D9) allowed evaluation of the development between day 9 (removal of the occlusive plasters) and day 15 (6 days after removal of the occlusive plasters). This development is representative of the epidermal cell renewal cycle. The greater the value, the higher the epidermal cell renewal.

SUMMARY

The comparative human studies show a considerably higher epidermal cell renewal rate from treatment with emulsions containing 3% by weight or 5% by weight Vitoptine® compared to treatment with emulsions containing 0.2% by weight or 0.5% by weight vitamin A palmitate.

Commercial Applications

The present invention also relates to cosmetic or dermopharmaceutical compositions for local application to the skin, the epithelial appendages and/or the mucosa which contain at least one protein fraction extracted from *Vigna aconitifolia* seeds as active component either on its own or in conjunction with at least one other active component.

This cosmetic composition may contain as sole active component or in conjunction with at least one other active component at least one extract of the above-mentioned type which is used to produce at least one of the particular biological effects described above or even several of those effects in combination.

The cosmetic or dermopharmaceutical composition according to the invention may contain between 0.001 and 30% by weight, preferably between 0.1 and 20% by weight and more particularly between 0.2 and 10% by weight of a protein-containing extract extracted from *Vigna aconitifolia* seeds (the extracts were obtained by one of the above-mentioned processes). The extract may be incorporated in suitable cosmetic vectors, for example liposomes, macro-, micro- and nanocapsules, macro-, micro- and nanoparticles and other analogous and known forms. The concentration of *Vigna aconitifolia* protein extracts to be used in the preparations may be reduced by virtue of the high activity of *Vigna aconitifolia* compared with the protein extract contents of other *Vigna* species.

The above-mentioned extracts may be used for skin care and hygiene applications (products for the face and body, day or night cosmetics, sun protection products, nourishing regenerating products, anti-wrinkle cosmetics, slimming aids and anti-ageing preparations) in the form of such preparations as, for example, lotions or shampoos, creams, foaming agents, soaps, sticks, gels, hydrogels, sprays, emulsions, protection products, repairing, softening, film-forming and photoprotective compositions; permanent wave products and hair colors.

The above-mentioned extracts may be used for the production of cosmetic and/or dermopharmaceutical preparations such as, for example, hair shampoos, hair lotions, foam baths, shower baths, creams, gels, lotions, alcoholic and aqueous/alcoholic solutions, emulsions, wax/fat compounds, stick preparations, powders or ointments, but mainly products for the face and body, day or night cosmetics, sun protection products, nourishing regenerating products, anti-wrinkle cosmetics, slimming aids and anti-ageing products. These preparations may also contain mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives.

Surfactants

Suitable surfactants are anionic, nonionic, cationic and/or amphoteric or zwitterionic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, a-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as Dicaprylyl Carbonate (Cetiol® CC) for example, Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE) for example, ring opening products of epoxidized fatty acid esters with polyols, silicone oils (cyclomethicone, silicon methicone types, etc.) and/or aliphatic or naphthenic hydrocarbons such as, for example, squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, onto $C_{12-22}$ fatty acids, onto alkyl phenols containing 8 to 15 carbon atoms in the alkyl group and onto alkylamines containing 8 to 22 carbon atoms in the alkyl group;

alkyl and/or alkenyl oligoglycosides containing 8 to 22 carbon atoms in the alk(en)yl group and ethoxylated analogs thereof;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate;

polymer emulsifiers, for example Pemulen types (TR-1, TR-2) of Goodrich;

polyalkylene glycols and glycerol carbonate.

Ethylene Oxide Addition Products

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations from DE 2024051 PS.

Alkyl and/or Alkenyl Oligoglycosides

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic fatty acids containing 12 to 22 carbon atoms such as, for example, palmitic acid, stearic acid or behenic acid and dicarboxylic acids containing 12 to 22 carbon atoms such as, for example, azelaic acid or sebacic acid.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N, N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizinq Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil., 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylidene)-camphor as described in EP 0693471 B1;
- 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);
- propane-1,3-diones such as, for example, 1-(4-tert.butylphenyl)-3-(4'-methoxyphenyl)-propane-1,3-dione;
- ketotricyclo(5.2.1.0)decane derivatives as described in EP 0694521 B1.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SÖFW-Journal 122, 543 (1996) and in Part. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methyl-ethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants

Antiperspirants reduce perspiration and thus counteract underarm wetness and body odor by influencing the activity of the eccrine sweat glands. Aqueous or water-free antiperspirant formulations typically contain the following ingredients:
astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,
   inflammation-inhibiting, skin-protecting or pleasant-smelling essential oils,
   synthetic skin-protecting agents and/or
   oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are
   glycerol;
   alkylene glycols such as, for example, ethylene glycol, diethylene glycol, propylene glycol, butylene glycol, hexylene glycol and polyethylene glycols with an average molecular weight of 100 to 1000 dalton;
   technical oligoglycerol mixtures with a degree of self-condensation of 1.5 to 10 such as, for example, technical diglycerol mixtures with a diglycerol content of 40 to 50% by weight;
   methylol compounds such as, in particular, trimethylol ethane, trimethylol propane, trimethylol butane, pentaerythritol and dipenta-erythritol;
   lower alkyl glucosides, particularly those containing 1 to 8 carbon atoms in the alkyl group, for example methyl and butyl glucoside;
   sugar alcohols containing 5 to 12 carbon atoms, for example sorbitol or mannitol,
   sugars containing 5 to 12 carbon atoms, for example glucose or sucrose;
   amino sugars, for example glucamine;
   dialcoholamines, such as diethanolamine or 2-aminopropane-1,3-diol.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetik-verordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat. Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The preparations may be produced by standard hot or cold processes and are preferably produced by the phase inversion temperature method.

Examples for the Production of Protein Extracts

I) Preparation of the Protein Extracts of *Vigna aconitifolia* Seeds

The proteins are prepared by the methods already described in FR 2796839 A1 for *Vigna trilobata* by any of the conventional techniques for the extraction of plant proteins, the preparation of concentrates or protein isolates or by purification (ultrafiltration, ion exchange chromatography, affinity chromatography, precipitation, adsorption) which are known to the expert on the subject.

However, the extraction process is preferably carried out with water or an aqueous solution at a given pH value (see Examples 6 and 7), optionally in conjunction with an ultrasound generator.

Various processes for the isolation and preparation of protein extracts from two different, divided quantities of *Vigna aconitifolia* seeds of Indian origin are described below as illustrative examples which are not intended to limit the invention in any way.

Example 1

180 g meal obtained by crushing dry *Vigna aconitifolia* seeds were added to 1.5 liters distilled water. After stirring for 15 minutes, the pH of the solution was adapted to the pH of 7.0 with sodium hydroxide. Extraction was carried out for 3 hours at room temperature by keeping the extraction pH at 7.0. After centrifuging for 10 mins. at 4,500 G, the beige substance floating on the surface was collected and then filtered to 0.5 μm. The extract can be freed from water by conventional techniques, for example spray drying, freeze drying or the like. After spray drying, the powder-like product obtained had a protein content (N×6.25) of 47.0% (extract 1).

Example 2

300 g meal obtained by crushing *Vigna aconitifolia* seeds were added to 2.5 liters distilled water and the solution was processed as in Example 1. 2.2 liters of a beige solution were obtained. The solution was adjusted to a pH of 4.5 with sulfuric acid and stirred for 30 minutes. The solution was then centrifuged for 30 mins. at 3,500 G. The deposit and the material floating on the surface were separately collected. The deposit was added as a solution to a volume of water which corresponded to 20% of the volume before formation of the deposit. The pH of the solution was adjusted with NaOH until it settled at 7.2. The solution was centrifuged again to separate the insoluble substances. 600 ml of a solution of a 3.8% dry extract were obtained and were freed from water by spray drying. After spray drying, the powder-like product obtained had a protein content (N×6.25) of 84.2% (extract 2).

Example 3

The substances floating on the surface obtained after deposition of the proteins at pH 4.5 in accordance with Example 2 were filtered to 0.5 μm. The clear solutions obtained were freed from water by spray drying. The powder obtained had a protein content of 17% to 21%.

Example 4

250 ml crude extract (pH 7.5) prepared in accordance with Example 1 were introduced into an Amicon 8200 ultrafiltration cell equipped with a 100,000 da ultrafiltration membrane (ref. YM 100, diameter 6 cm). The solution was concentrated to 55 ml (pressure of the compressed air 3 bar). Permeate P1 and retentate R1 were collected. 150 ml distilled water were added to the retentate and the solution was again concentrated to 50 ml (retentate R2). Retentate R2 was freed from water by freeze-drying. A fraction with a protein content of 84.5% (N×6.25) was obtained.

Example 5

A protein concentrate was prepared as in Example 2 from 350 g seeds, the initial extraction being carried out at a meal-to-solvent ratio of 1:15. The deposit was dissolved in 1.5 liters distilled water at pH 7.5. 500 ml protein concentrate solution containing 60.5 g/l proteins (N×6.25) were ultimately obtained. The proteins were hydrolyzed with an alkaline protease (2.5% in relation to the proteins of the solution) at pH 7.5-8.5. The hydrolysis was carried out for 2 hours at an optimized temperature and optimized pH of the enzyme used (the optimized values are known to the expert). The enzyme was inactivated by heating to 100° C. for at least 10 minutes. After cooling to room temperature, the solution is centrifuged and the filtered to 0.22 µm. 450 ml of a dark, clear filtrate containing 6.53% dry extract (proteins 45.2 g/l) were obtained. The powder obtained after spray drying had a protein content of 72.0% (extract 3).

Analysis of the fractions extracted by these various methods by gel permeation in a Superose 12 HR column enabled at least 10 protein fractions to be identified. The molecular weight distribution of the proteins was as follows: 80%<5,000 da and 5,000 da<20%<50,000 da.

The constituents of the hydrolyzate obtained as described in Example 5 had an average molecular weight of 3,500 da.

The extracts obtained in accordance with above Examples can be directly used in liquid form or after drying by conventional techniques (spray drying, freeze drying). The protein fractions obtained may be used either in their original form without any modification of the structures or in the form of one or more natural compounds of at least two, or all, extracted fractions with different visible molecular weights which correspond to different chromatogram peaks, as shown in the accompanying drawings, and which are naturally present in the seeds (total or partial protein extract) or in isolated form.

The protein fractions may be used in compositions in a form modified or functionalized by any of the following treatments:
- polymerization of the original proteins;
- chemical hydrolysis of the original proteins;
- enzymatic hydrolysis of the original proteins by proteases of animal, vegetable, microbial or fungal origin: pepsin, trypsin, chymotrypsin, papain, pronase, bromelain, endoproteinase, thermitase, proteases of *Bacillus subtilis, Aspergillus niger, Aspergillus oryzae* (subtilisin, alkalase, neutrase);
- microbial modification by various microorganisms, for example yeasts (*Saccharomyces*), molds (*Aspergillus*), bacteria (*Bacillus* and the like) using proteins of *Vigna aconitifolia* as fermentation substrate;
- chemical or enzymatic functionalization by such processes as succinylation or phosphorylation;
- quaternization;
- grafting of the saccharidic or lipidic molecules or any other chemical modification by grafting.

Example 6

Preferred Production Process

The extracts according to the invention are preferably produced by extraction of the seeds with water for 1 to 6 hours and preferably for 2 to 4 hours at 30° C. to 70° C., preferably at 35° C. to 60° C. and more particularly at 40° C. to 50° C. Residues and solvent are separated and, after heating for 0.5 to 3 hours and preferably for 1 to 2 hours at 70 to 90° C. and preferably at 75 to 85° C., the pH is adjusted to pH 5-7 and preferably to pH 5.5 to 6.5, followed by centrifuging and filtration. The extract obtained has a nitrogen content of at least 0.4, preferably at least 0.5 and more particularly above 0.6% by weight and the following molecular weight distribution: 80%<5,000 da and 20%>5,000 da and <50,000 da (molecular weight determined with Superose® 12 HR, FPLC, Pharmacia). Other auxiliaries, such as preservatives, antioxidants and polyols, may be added to the extract.

Example 7

Preparation of the Product VITOPTINE® (Laboratoires Sérobiologiques) with *Vigna aconitifolia* Extract Preparation 50 kg of *Vigna aconitifolia* seeds were extracted with 200 kg-300 kg water for 3 to 4 hours at 40 to 50° C. Residues and solvent were separated and, after heating for 1 hour at 80° C., the pH was adjusted to pH 6, followed by centrifuging (3,500 G, 75 kg/h) and filtration. The extract obtained had a nitrogen content of 0.5 to 1% by weight. The components water, glycerol, sodium citrate and preservative were added to the extract with stirring at 60° C., after which the extract was adjusted to pH 6 and refiltered.

TABLE 5

Composition of the protein-extract-containing formulation of Vigna aconitifolia for use in cosmetic and/or dermopharmaceutical preparations (quantities in % by weight).

| Constituents | Composition according to the invention | Preferable | Particularly preferable |
|---|---|---|---|
| Vigna aconitifolia seed extract | 40-70 | 50-65 | 54-62 |
| Glycerol | 1-50 | 10-40 | 15-30 |
| Sodium citrate | 0.01-3 | 0.1-2 | 0.5-1.5 |
| Preservative (chlorphenesin, methylparaben) | q.s. | q.s. | q.s. |
| Water | to 100.0 | to 100.0 | to 100.0 |

The *Vigna aconitifolia* extracts prepared in accordance with Example 6—in combination with the auxiliaries described in Example 5—are particularly suitable for use in cosmetic and/or dermopharmaceutical preparations because they represent storable concentrates which are easy to process into formulations and which lead to physicochemically stable and dermatologically highly compatible preparations.

Formulation Examples

Various cosmetic compositions according to the invention are illustrated by the following Examples.

Example 1

| Regeneration cream - (dist. water to 100.0, quantities in % by weight) | |
|---|---|
| Fatty phase | |
| Ceteareth 25 | 2.00 |
| Ceteareth 6 and stearyl alcohol | 1.00 |
| Cetyl alcohol | 4.00 |
| Glycol stearate | 4.00 |
| Vaseline | 5.00 |
| MCT-Triglyceride, Miglyol | 5.00 |
| Aqueous phase | |
| Glycerol | 10.00 |
| Vigna aconitifolia protein extract of Process Example 1 | 2.00 |
| Distilled water | 8.50 |
| Elestab 4112 preservative (Laboratoires Sérobiol.) | 0.40 |
| Perfume | q.s. |

The fatty phase was melted at 80° C. The aqueous phase was also heated to 80° C. and the Elestab 4112 was dissolved therein. The mother solution of the *Vigna* extract Vitoptine® was separately prepared, the fatty phase was added to the aqueous phase with stirring (turbine agitator) and the Vitoptine® was then introduced at ca. 50° C. Stirring was then continued until the product had cooled.

Example 2

Cream for sensitive skin types and for the treatment of inflamed or damaged skin (dist. water to 100.0, quantities in % by weight)

Fatty phase

| | |
|---|---|
| Glycol stearate | 14.00 |
| Octyl dodecanol | 6.00 |
| Dibutyl adipate | 6.00 |
| Ceteareth 12 | 1.50 |
| Ceteareth 20 | 1.50 |

Aqueous phase

| | |
|---|---|
| PVP (polyvinyl pyrrolidone) | 0.50 |
| Glycerol | 4.00 |
| Elestab 388 (Laboratoires Sérobiologiques) | 2.00 |
| Vigna aconitifolia of Process Example 2 | 3.00 |
| Distilled water | 9.00 |
| Perfume | 0.20 |

The fatty phase was melted at 80° C. The aqueous phase was also heated to 80° C. and the Elestab 388 and PVP were dissolved therein. The Vitoptine® was separately prepared, the fatty phase was added to the aqueous phase with stirring (turbine agitator) and the Vitoptine® was then introduced at ca. 50° C. Stirring was then continued until the product had cooled.

Further proposals for formulations containing *Vigna aconitifolia* extract VITOPTINE® (Laboratoires Sérobiologiques) are set out in Tables 5a and 5b.

TABLE 5a

Cosmetic preparations (quantities in % by weight)

| Composition (INCI) | 1 | 2 | 3 |
|---|---|---|---|
| Emulgade ® SE Glyceryl Sterate (and) Ceteareth 12/20 (and) Cetearyl Alcohol (and) Cetyl Palmitate | 5.0 | 5.0 | — |
| Lameform ® TGI Polyglyceryl-3 Isostearate | — | — | 4.0 |
| Monomuls ® 90-O 18 Glyceryl Oleate | — | — | 2.0 |
| Cetiol ® OE Dicaprylyl Ether | — | — | 5.0 |
| Cetiol ® PGL Hexyldecanol (and) Hexyldecyl Laurate | — | — | 10.0 |
| Cetiol ® SN Cetearyl Isononanoate | 3.0 | 3.0 | — |
| Cetiol ® V Decyl Oleate | 3.0 | 3.0 | — |
| Myritol ® 318 Coco Caprylate Caprate | — | — | 5.0 |
| Bees Wax | — | — | 7.0 |
| Nutrilan ® Keratin W Hydrolyzed Keratin | 40.0 | 60.0 | — |
| Gluadin ® WK Sodium Cocoyl Hydrolyzed Wheat Protein | — | — | 5.0 |

TABLE 5a-continued

Cosmetic preparations (quantities in % by weight)

| Composition (INCI) | 1 | 2 | 3 |
|---|---|---|---|
| Magnesium Sulfate Hepta Hydrate | — | — | 1.0 |
| Glycerin (86% by weight) | 3.0 | 3.0 | 5.0 |
| Vitoptine ® | 2.0 | 5.0 | 3.0 |
| Aqua conservata | to 100.0 | to 100.0 | to 100.0 |

(1) Soft cream,
(2) Moisturizing emulsion,
(3) Night cream

TABLE 5b

Cosmetic preparations (quantities in % by weight)

| Composition (INCI) | 4 | 5 | 6 | 7 |
|---|---|---|---|---|
| Dehymuls ® PGPH Polyglyceryl-2 Dipolyhydroxystearate | 2.0 | 3.0 | — | — |
| Lameform ® TGI Polyglyceryl-3 Diisostearate | 4.0 | 1.0 | — | — |
| Eumulgin VL 75 Polyglyceryl-2 Dipolyhydroxystearate (and) Lauryl Glucoside (and) Glycerin | — | — | 3.5 | — |
| Bees Wax | 3.0 | 2.0 | — | — |
| Cutina ® GMS Glyceryl Stearate | — | — | 2.0 | 4.0 |
| Lanette ® O Cetearyl Alcohol | — | — | 4.0 | 1.0 |
| Antaron ® V 216 PVP/Hexadecene Copolymer | — | — | 3.0 | 2.0 |
| Plantaren ® 818 Cocoglycerides | 5.0 | — | 6.0 | 5.0 |
| Finsolv ® TN C12/15 Alkyl Benzoate | — | 6.0 | — | 2.0 |
| Dioctyl Carbonate | 5.0 | 4.0 | 5.0 | 6.0 |
| Cetiol ® J 600 Oleyl Erucate | 2.0 | — | 3.0 | 4.0 |
| Cetiol ® OE Dicaprylyl Ether | 3.0 | — | 1.0 | — |
| Mineral Oil | — | 4.0 | 2.0 | — |
| Cetiol ® PGL Hexadecanol (and) Hexyldecyl Laurate | — | 7.0 | — | — |
| Panthenol/Bisabolol | 1.2 | 1.2 | 1.2 | 1.2 |
| Copherol ® F 1300 Tocopherol/Tocopheyl Acetate | 0.5 | 1.0 | 1.0 | 2.0 |
| Neo Heliopan ® Hydro Sodium Phenylbenzimidazole Sulfonate | 3.0 | — | — | — |
| Neo Heliopan ® 303 Octocrylene | — | 5.0 | 4.0 | 10.0 |
| Neo Heliopan ® BB Benzophenone-3 | 1.5 | — | — | — |
| Neo Heliopan ® E 1000 Isoamyl p-Methoxycinnamate | 5.0 | — | 2.0 | — |
| Neo Heliopan ® AV Octyl Methoxycinnamate | 4.0 | — | 3.0 | 2.0 |
| Uvinul ® T 150 Octyl triazone | 2.0 | 4.0 | 1.0 | 3.0 |
| Zinc Oxide | — | 6.0 | — | 5.0 |
| Titanium Dioxide | — | 2.0 | — | — |
| Glycerin (86% by weight) | 5.0 | 5.0 | 5.0 | 5.0 |
| VITOPTINE ® | 3.0 | 2.0 | 5.0 | 4.0 |
| Aqua conservata | to 100.0 | to 100.0 | to 100.0 | to 100.0 |

(4) W/O sun protection cream,
(5) W/O sun protection lotion,
(6) O/W sun protection cream,
(7) O/W sun protection lotion

The invention claimed is:

1. A topical cosmetic and/or dermopharmaceutical composition for improving signs of aging in skin, improving skin quality, treating inflamed skin or treating damaged skin in humans comprising:
an effective amount of a) a protein containing extract from *Vigna aconitifolia* plant obtained by extracting seeds of the *Vigna aconitifolia* plant with water or an aqueous solution at 30° C. to 70° C. to obtain a solvent extract and a residue, separating the solvent extract from the residue, heating the solvent extract at 70° C. to 90° C., adjusting the solvent extract to pH 5-7, and centrifuging and filtering the solvent extract to obtain the protein containing extract and b) at least one polyol.

2. The composition of claim 1, wherein the protein containing extract contains at least one soluble protein fraction extracted from seeds of the *Vigna aconitifolia* plant.

3. The composition of claim 1, wherein the protein containing extract is present in the composition in an amount of from about 0.001 to 30% by weight, based on the weight of the composition.

4. The composition of claim 1, wherein the protein containing extract is present in the composition in an amount of from about 0.1 to 20% by weight, based on the weight of the composition.

5. The composition of claim 1, wherein the protein containing extract is present in the composition in an amount of from about 0.2 to 10% by weight, based on the weight of the composition.

6. A method of improving signs of aging in skin, improving skin quality, treating inflamed skin or treating damaged skin in a person in need thereof comprising:
topically applying to skin of the person a composition comprising a therapeutically effective amount of a) a protein containing extract from a *Vigna aconitifolia* plant produced by a process consisting essentially of extracting seeds of the *Vigna aconitifolia* plant with water or an aqueous solution at 30° C. to 70° C. to obtain a solvent extract and a residue, separating the solvent extract from the residue, heating the solvent extract at 70° C. to 90° C., adjusting the solvent extract to pH 5-7, and centrifuging and filtering the solvent extract to obtain the protein containing extract and b) a polyol.

7. The method of claim 6, wherein the protein containing extract contains at least one soluble protein fraction extracted from seeds of the *Vigna aconitifolia* plant.

8. The method of claim 6, wherein the protein containing extract is present in the composition in an amount of from about 0.001 to 30% by weight, based on the weight of the composition.

9. The method of claim 6, wherein the protein containing extract is present in the composition in an amount of from about 0.1 to 20% by weight, based on the weight of the composition.

10. The method of claim 6, wherein the protein containing extract is present in the composition in an amount of from about 0.2 to 10% by weight, based on the weight of the composition.

11. The composition of claim 1, wherein the composition comprises from about 1 to about 50% by weight of the polyol.

12. The composition of claim 11, wherein the polyol comprises glycerol.

13. The composition of claim 1, wherein the composition comprises:
a) from about 40 to about 70% by weight of the protein containing extract of the *Vigna aconitifolia* plant, and
b) from about 1 to about 50% by weight of the polyol.

14. A topical cosmetic and/or dermopharmaceutical composition for improving signs of aging in skin, improving skin quality, treating inflamed skin or treating damaged skin in humans comprising:
an effective amount of a) a protein containing extract from *Vigna aconitifolia* plant obtained by extracting seeds of the *Vigna aconitifolia* plant with water or an aqueous solution at 30° C. to 70° C. to obtain a solvent extract and a residue, separating the solvent extract from the residue, heating the solvent extract at 70° C. to 90° C., adjusting the solvent extract to pH 5-7, and centrifuging and filtering the solvent extract to obtain the protein containing extract and b) a cosmetically and/or dermopharmaceutically acceptable auxiliary.

15. The composition of claim 14, wherein the protein containing extract is present in the composition in an amount of from about 0.001 to 30% by weight, based on the weight of the composition.

16. The composition of claim 1, wherein the seeds are extracted at 40° C. to 50° C. and the pH of the solvent extract is adjusted to pH 5.5 to 6.5.

17. The composition of claim 1, wherein the at least one polyol includes glycerol.

18. The composition of claim 17, further comprising an antioxidant and a preservative.

19. The composition of claim 15, wherein the composition comprises from 50 to 65% by weight of the protein containing extract and from 10 to 40% by weight of the polyols.

* * * * *